United States Patent [19]

Fancher

[11] 4,197,295

[45] Apr. 8, 1980

[54] PYRAZOLE PHOSPHATES AND PHOSPHONATES - INSECTICIDES

[75] Inventor: Llewellyn W. Fancher, Orinda, Calif.

[73] Assignee: Stauffer Chemical Company, Westport, Conn.

[21] Appl. No.: 947,803

[22] Filed: Oct. 2, 1978

[51] Int. Cl.$^2$ .................... A01N 9/36; C07F 9/16
[52] U.S. Cl. ............................ 424/200; 548/378
[58] Field of Search .................... 548/378; 424/200

[56] References Cited

U.S. PATENT DOCUMENTS

| | | | |
|---|---|---|---|
| 3,185,699 | 5/1965 | Sherlock | 548/378 |
| 3,658,800 | 4/1972 | Beriger | 424/200 |
| 3,780,056 | 12/1973 | Singhal et al. | 424/200 |
| 3,806,560 | 4/1974 | Kishino et al. | 424/200 |
| 3,979,512 | 9/1976 | Stölzer et al. | 424/200 |
| 3,997,526 | 12/1976 | Satomi et al. | 424/200 |
| 4,015,974 | 4/1977 | Satomi et al. | 424/200 |
| 4,094,974 | 6/1978 | Fancher | 424/200 |
| 4,104,375 | 8/1978 | Fancher | 424/200 |

FOREIGN PATENT DOCUMENTS 1184552 12/1964 Fed. Rep. of Germany ........... 548/378

*Primary Examiner*—Alan L. Rotman
*Assistant Examiner*—Natalia Harkaway
*Attorney, Agent, or Firm*—Harry A. Pacini

[57] ABSTRACT

Compounds having the formula

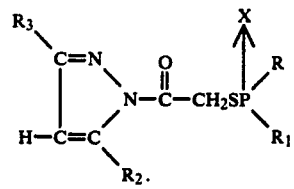

wherein X is oxygen or sulfur, R is selected from the group consisting of alkyl and alkoxy, $R_1$ is alkoxy, $R_2$ is selected from the group consisting of hydrogen and methyl and $R_3$ is selected from the group consisting of hydrogen, methyl and phenyl; these compounds are active as insecticides.

57 Claims, No Drawings

PYRAZOLE PHOSPHATES AND PHOSPHONATES - INSECTICIDES

BRIEF DESCRIPTION OF THE INVENTION

This invention relates to certain novel heterocyclic compounds and their utility as insecticides. More particularly, the compounds are certain pyrazole phosphates and phosphonates.

The compounds of this invention that are useful as insecticides are those having the following formula:

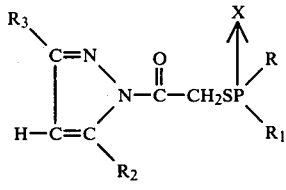

wherein X is oxygen or sulfur, R is selected from the group consisting of alkyl having 1 to 6 carbon atoms, inclusive, and alkoxy having 1 to 6 carbon atoms, inclusive; $R_1$ is alkoxy having 1 to 6 carbon atoms, inclusive; $R_2$ is selected from the group consisting of hydrogen and methyl; and $R_3$ is selected from the group consisting of hydrogen, methyl and phenyl. Included among the compounds of the invention are the compounds wherein X is oxygen, R is alkoxy, $R_2$ is methyl and $R_3$ is methyl; X is oxygen, R is alkoxy, $R_2$ is hydrogen and $R_3$ is methyl; X is sulfur, R is alkoxy, $R_2$ is methyl and $R_3$ is methyl; X is sulfur, R is alkyl, $R_2$ is hydrogen and $R_3$ is methyl; X is sulfur, R is alkoxy, $R_2$ is hydrogen and $R_3$ is methyl; X is sulfur, R is alkyl, $R_2$ is methyl and $R_3$ is phenyl; X is sulfur, R is alkoxy, $R_2$ is methyl and $R_3$ is phenyl; and X is oxygen, R is alkoxy, $R_2$ is methyl and $R_3$ is phenyl.

These above-described compounds are useful as insecticides, when used in an insecticidally effective amount. By "insecticidally effective amount" is meant the amount of the herein-disclosed compounds which when applied in any conventional manner to the habitat of insects, the feedstuffs of insects, or the insects themselves, will kill or substantially injure a significant portion thereof.

DETAILED DESCRIPTION OF THE INVENTION

General Method of Preparation

A. Intermediates

Pyrazoles as intermediates can be prepared by the cyclo condensation of a dicarbonyl compound, such as acetyl acetone, with hydrazine (see *Organic Synthesis*, Vol. 31, page 43). In some instances, the pyrazole intermediates may be purchased from a chemical supplier.

Chloroacetyl pyrazoles as intermediates can be conveniently prepared by the following general reaction. The pyrazole can be chloroacetylated by the reaction of chloroacetic anhydride with a pyrazole in an inert solvent, such as tetrahydrofuran. Chloroacetic anhydride is convenient but chloroacetyl chloride and a base will also be operable. The chloroacetyl pyrazole can be isolated by treatment with water, filtration of the resulting solid followed by drying.

The final product is prepared by reacting a chloroacetyl pyrazole with a phosphoric or phosphonic acid, neutralized with a base such as triethylamine, or reacting with a preformed salt of the acid, such as the sodium, potassium, or ammonium salt, in the presence of an inert solvent. Dimethyl formamide is the preferred solvent, since the chloroacetyl pyrazole has limited solubility in other non-reactive solvents. The reaction is carried out at or near room temperature to prevent side reactions, which can occur at higher temperatures. The product is isolated by dilution with a water insoluble solvent, such as benzene or toluene. This is followed by washing with water, drying (anhydrous magnesium sulfate), filtering and evaporation of the solvent.

Various pyrazole phosphates and phosphonates can be prepared by using the above reactants and procedures. The following examples are further illustrations of the preparation of the compounds of this invention.

EXAMPLE 1

Preparation of 1-O,O-diethylphosphorodithioylacetyl-3,5-dimethyl-pyrazole

The O,O-diethylphosphorodithioic acid, 3.72 grams (0.02 mole) $(C_2H_5O)_2P(S)SH$, was dissolved in 25 milliliters of dimethyl formamide. This acid solution was neutralized with triethylamine, 2.01 grams (0.02 mole) while cooling the vessel. To this solution was added 2.59 grams (0.015 mole) of 1-chloroacetyl-3,5-dimethylpyrazole. The reaction mixture was stirred at ambient temperature for four hours. At that time the reaction mixture was diluted with 150 milliliters of benzene followed by two washes of 100 milliliters of dilute sodium chloride solution. The organic phase was separated and dried over magnesium sulfate, filtered and the organic solvent removed under vacuum. There was obtained 4.71 grams of the title product, a light yellow liquid, $n_D^{30}$ 1.5355. Product exhibited solubility in acetone. NMR analysis confirmed the structure.

EXAMPLE 2

Preparation of the intermediate 1-chloroacetyl-3,5dimethylpyrazole.

In 50 milliliters of tetrahydrofuran, there was slurried 19.2 grams (0.2 mole) of 3,5-dimethylpyrazole. To this slurry was added 37.6 grams (0.22 mole) of chloroacetic anhydride at one time. A solution resulted. The temperature rose from 17° C. to 34° C. The solution was allowed to stand for one hour at ambient temperature followed by reflux on a steam bath for 5 minutes. After standing overnight, the reaction mixture was poured into 50 milliliters of cold water. A solid material percipitated. To hasten the reaction of chloroacetic anhydride with water, the mixture was heated to 50° C. on a steam bath. After standing for 15 minutes, the solution was cooled to 15° C., filtered and washed with cold water. After washing 2 additional times with n-hexane, the product was dried at 50° C. for 1 hour and then at 40° C. There was obtained 30.1 grams of the title compound as a fine needle-like white solid, m.p. 72°–75° C. soluble in acetone. The structure was confirmed by nuclear magnetic resonance.

Preparation of 1-ethyl,O-ethylphosphonodithioylacetyl3,5-dimethyl-pyrazole.

In a similar reaction given in Example 1, ethyl,O-ethylphosphonodithioic acid (3.40 grams, 0.02 mole) was dissolved in 25 milliliters of dimethyl formamide with stirring. The solution was cooled and neutralized with 2.01 grams (0.02 mole) of triethylamine at a temperature below 30° C. To this solution was added 2.59 grams (0.15 mole) of 1-chloroacetyl-3,5-dimethylpyrazole). This mixture was stirred at ambient temperature for 4 hours. After 4 hours, the reaction mixture was diluted with 180 milliliters of benzene, washed with two-100 milliliter portions of dilute sodium chloride solution, and dried over magnesium sulfate. After filtering and evaporating the organic solvent under vacuum, there was obtained 4.54 grams of the title compound as a yellow liquid, $n_D^{30}$ 1.5482. The structure was confirmed by nuclear magnetic resonance.

EXAMPLE 3

Preparation of 1-ethyl,O-isobutyl phosphonodithioylacetyl-3,5-dimethylpyrazole.

In 25 milliliters of dimethyl formamide, 3.96 grams (0.02 mole) of ethyl,O-isobutyl phosphonodithioic acid was dissolved. This was neutralized with 2.01 grams (0.02 mole) of triethylamine with cooling below 30° C. There was added to this solution 2.59 grams (0.015 mole) of the intermediate 1-chloroacetyl-3,5-dimethylpyrazole. The reaction mixture was stirred at ambient temperature for 4 hours. At the end of this time, the reaction mixture was diluted with 150 milliliters of benzene and washed with two-150 milliliter portions of dilute sodium chloride solution. The organic portion was separated and dried over magnesium sulfate, filtered and the organic solvent evaporated under vacuum. There was obtained a yellow liquid, 4.70 grams of the title compound, $n_D^{30}$ 1.5357. The structure was confirmed by nuclear magnetic resonance.

EXAMPLE 4

Preparation of 1-O,O-diethylphosphonomonothioylacetyl3,5-dimethylpyrazole.

In 25 milliliters of dimethyl formamide, 4.16 grams (0.02 mole) of potassium O,O-diethylphosphonomonothioate was dissolved. To this solution was added 2.59 grams (0.015 mole) of 1-chloroacetyl-3,5-dimethylpyrazole and stirred at room temperature for 4 hours. The reaction mixture was diluted with 100 milliliters of benzene and washed with 2 portions of 100 milliliters each dilute sodium chloride solution. After separation of the organic phase, it was dried over magnesium sulfate, filtered and the organic solvent evaporated under vacuum. There was obtained 4.5 grams of the title compound as an amber colored liquid, $n_D^{30}$ 1.5075. The structure was confirmed by nuclear magnetic resonance.

EXAMPLE 5

Preparation of 1-N-O,O-diethylphosphorodithioylacetyl-3-phenyl-5-methyl-pyrazole.

By the same procedure as in Example 3, 3.88 grams (0.019 mole) of 90 percent O-ethyl phosphonodithioic acid was dissolved in 25 milliliters of dimethyl formamide and neutralized with 1.9 grams (0.019 mole) of triethylamine with cooling below 25° C. To this solution was added 3.28 grams (0.014 mole) 1-chloroacetyl-3-phenyl,5-methyl-pyrazole, and the reaction mixture stirred at ambient temperature for 4 hours. At the end of this time, the reaction mixture was diluted with 100 milliliters of toluene and washed with two portions of 75 milliliters each of dilute sodium chloride solution. After separation, the organic portion was dried over magnesium sulfate, filtered and the organic solvent evaporated in vacuo. There was obtained 5.26 grams of the title compound, $n_D^{30}$ 1.5774. The structure was confirmed by nuclear magnetic resonance.

EXAMPLE 6

Preparation of 1-N-O,O-diethylphosphoromonothioylacetyl-3-phenyl-5-methyl-pyrazole.

In 25 milliliters of dimethyl formamide, 2.8 grams (0.0135 mole) of potassium O,O-diethylphosphoromonothioate was dissolved. To this solution was added 2.04 grams (0.0087 mole) of 1-chloroacetyl-3-phenyl,5-methyl-pyrazole. The reaction mixture was stirred at ambient temperature for 4 hours. At the end of this time, the mixture was diluted with 100 milliliters of toluene and washed with two portions of 75 milliliters each of water. After separation, the organic phase was dried over magnesium sulfate, filtered and evaporated in vacuo. There was obtained 2.8 grams of the title compound, an amber colored liquid, $n_D^{30}$ 1.5615. The structure was confirmed by nuclear magnetic resonance.

The following is a table of representative and illustrative compounds that can be prepared according to the aforementioned procedures. Compound numbers have been assigned to each compound and used for identification throughout the balance of the application.

TABLE I

| Compound Number | X | R | $R_1$ | $R_2$ | $R_3$ | m.p. or $n_D^{30}$ |
|---|---|---|---|---|---|---|
| 1 | S | $OC_2H_5$ | $OC_2H_5$ | $CH_3$ | $CH_3$ | 1.5355 |
| 2 | S | $OCH_3$ | $OCH_3$ | $CH_3$ | $CH_3$ | 1.5496 |
| 3 | S | $C_2H_5$ | $OC_2H_5$ | $CH_3$ | $CH_3$ | 1.5482 |
| 4 | S | $C_2H_5$ | $O$-$i$-$C_3H_7$ | $CH_3$ | $CH_3$ | 1.5405 |
| 5 | S | $C_2H_5$ | $O$-$i$-$C_4H_9$ | $CH_3$ | $CH_3$ | 1.5357 |
| 6 | S | $C_2H_5$ | $OC_2H_5$ | H | $CH_3$ | 1.5551 |
| 7 | S | $C_2H_5$ | $O$-$i$-$C_3H_7$ | H | $CH_3$ | 1.5434 |
| 8 | S | $C_2H_5$ | $O$-$i$-$C_4H_9$ | H | $CH_3$ | 1.5330 |
| 9 | O | $OC_2H_5$ | $OC_2H_5$ | $CH_3$ | $CH_3$ | 1.5075 |
| 10 | S | $OCH_3$ | $OCH_3$ | H | $CH_3$ | 1.5480 |
| 11 | O | $OC_2H_5$ | $OC_2H_5$ | H | $CH_3$ | 1.5055 |
| 12 | S | $OC_2H_5$ | $OC_2H_5$ | H | $CH_3$ | 1.5370 |
| 13 | S | $C_2H_5$ | $OC_2H_5$ | $CH_3$ | Φ | 86°–90° C. |
| 14 | S | $OC_2H_5$ | $OC_2H_5$ | $CH_3$ | Φ | 1.5774 |
| 15 | S | $C_2H_5$ | $O$-$i$-$C_3H_7$ | $CH_3$ | Φ | 77°–80° C. |
| 16 | S | $C_2H_5$ | $O$-$i$-$C_4H_9$ | $CH_3$ | Φ | 1.5752 |
| 17 | S | $OCH_3$ | $OCH_3$ | $CH_3$ | Φ | 1.5980 |
| 18 | O | $OC_2H_5$ | $OC_2H_5$ | $CH_3$ | Φ | 1.5615 |
| 19 | S | $OC_2H_5$ | $OC_2H_5$ | $CH_3$ | H | |
| 20 | O | $OC_2H_5$ | $OC_2H_5$ | $CH_3$ | H | |
| 21 | S | $C_2H_5$ | $O$-$i$-$C_3H_7$ | $CH_3$ | H | |
| 22 | O | $C_2H_5$ | $O$-$i$-$C_3H_7$ | $CH_3$ | H | |
| 23 | S | $OC_2H_5$ | $OC_2H_5$ | H | $CH_3$ | |
| 24 | O | $OC_2H_5$ | $OC_2H_5$ | H | $CH_3$ | |
| 25 | S | $C_2H_5$ | $O$-$i$-$C_4H_9$ | $CH_3$ | Φ | |
| 26 | O | $C_2H_5$ | $O$-$i$-$C_4H_9$ | $CH_3$ | Φ | |
| 27 | S | $OC_2H_5$ | $OCH_3$ | H | Φ | |
| 28 | O | $OCH_3$ | $OCH_3$ | H | Φ | |
| 29 | S | $OC_2H_5$ | $OC_2H_5$ | H | H | |
| 30 | S | $C_2H_5$ | $OC_2H_5$ | H | H | |
| 31 | O | $OC_2H_5$ | $OC_2H_5$ | H | H | |

INSECTICIDAL EVALUATION TESTS

The term "insect" is used herein in its broad common usage to include spiders, mites, ticks and like pests which are not in the strict biological sense classified as insects. The term "insect" is used to refer not only to those small invertebrate animals belonging mostly to the class Insecta, comprising six-legged usually winged forms, as beetles, bugs, bees, flies, and so forth, but also to other allied classes of arthropods whose members are wingless and usually have more than six legs, as spiders, mites, ticks, centipedes, and wood lice.

The following insect species were used in evaluation tests for insecticidal activity according to the following procedures.

A. Housefly [*Musca domestica* (L.)]

The test compound is diluted in acetone and an aliquot is pipetted onto the bottom of a 55×15 millimeter aluminum dish. To insure even spreading on the bottom of the dish, one milliliter of acetone containing 0.02% peanut oil is added. After all the solvent was evaporated, the dish is placed in a circular cardboard cage containing twenty-five one-day-old female houseflies. The cage is covered on the bottom with cellophane and the top with tulle netting, and contains a sugar-water saturated cotton plug for maintenance of the flies. Mortality is recorded after 48 hours. The primary screening level for this test is 100 micrograms of the test compound per 25 female houseflies.

B. Lygus bug [*Lygus hesperus* (Knight)]

The test compound is dissolved in a 50—50 acetone-water solution. Two milliliters of the solution are sprayed through a hand spray gun into a circular cardboard cage covered on the bottom with cellophane and the top with tulle netting, containing one string bean pod and ten adult lygus bugs. Percent mortality is recorded after 48 hours. The primary screening level for this test is 0.05% by weight of the test compound in the acetone-water solution.

C. Direct Spray Assay on Black Bean Aphid [*Aphis fabae* (Scop.)]

A nasturtium plant (*Tropaeolum sp.*), approximately 5 centimeters tall, is transplanted into sandy loam soil in a 3-inch clay pot and infested with 25–50 black been aphids of mixed ages. Twenty-four hours later the plant is sprayed, to the point of runoff, with a 50—50 acetone-water solution of the test chemical. The treated plant is held in the greenhouse and mortality is recorded after 3 days. The primary screening level for this test is 0.05% by weight of the test compound in the acetone-water solution.

D. Black Bean Aphid Systemic Evaluation Test

This test evaluates the root absorption and upward translocation of the candidate systemic compound. The bean aphid (BA) [*Aphis fabae* (Scop.)] was employed in the test for systemic activity. Young nasturtium plants were used as the host plants for the bean aphid. The host plants were transplanted into one pound of soil that had been treated with the candidate compound. Immediately after planting in the treated soil, the plants were infested with the aphids. Concentrations of toxicant in the soil ranged from 10 ppm downward until an LD-50 value was obtained. Mortality was recorded after 72 hours. The percentage of kill of the test species was determined by comparison with control plants placed in untreated soil. The LD-50 values were calculated.

E. Direct Spray Assay on Green Peach Aphid [*Myzus persicae* (Sulzer)]

A radish plant (*Rhaphanus sativus*), approximately 2 centimeters tall, is transplanted into sandy loam soil in a 3-inch clay pot and infested with 25-50 green peach aphids of mixed ages. Twenty-four hours later the plant is sprayed, to the point of runoff, with a 50—50 acetone-water solution of the test compound. The treated plant is held in a greenhouse and mortality is recorded after 3 days. The primary screening level for this test is 0.05% by weight of the test compound in the acetone-water solution.

F. German Cockroach [*Blatella germanica* (Linne)]

Test compounds are diluted in a 50—50 acetone-water solution. Two milliliters of the solution are sprayed through a hand spray gun into circular cardboard cages containing ten one-month-old German cockroach nymphs. The test cages are covered on the bottom with cellophane and the top with tulle netting. Percent mortality is recorded 7 days later. Test concentrations range from 0.1% down to that at which approximately 50% mortality occurs.

G. Saltmarsh Caterpillar [*Estigmene acrea* (Drury)]

A test solution is prepared by dissolving the test compound in a 50—50 acetone-water solution. A section of a curly dock (*Rumex crispus*) leaf, approximately 2.5 centimeters wide and 4 centimeters long, is immersed in the test solution for 2-3 seconds then placed on a wire screen to dry. The dried leaf was then place in a petri dish containing a moistened piece of filter paper, and infested with five second-instar saltmarsh caterpillar larvae. Mortality of the larvae is recorded 48 hours later. If surviving larvae are still present, a piece of synthetic media is added to the dish and the larvae are observed for an additional five days in order to detect delayed effects of the test compound. The primary screening level for this test is 0.05% by weight of the test compound in the solution.

H. Cabbage Looper [*Trichoplusia ni* (Hubner)]

The procedure for cabbage looper larvae is the same as that used for saltmarsh caterpillar larvae, except that a cotyledon of hyzini squash (*Calabacita abobrinha*) of approximately the same size as the curly dock leaf section is used in place of the latter. The primary screening level for this test is 0.1% by weight of the test compound in the solution.

I. Tobacco Budworm [*Heliothis virescens* (F.)]

Larvae of the tobacco budworm are used in this test in a procedure identical to that used for saltmarsh caterpillar larvae, except that a Romaine lettuce (*Latucs sativa*) leaf section of approximately the same size as the curly dock leaf section is used in place of the latter. The primary screening level for this test is 0.1% by weight of the test compound in the solution.

J. Southern House Mosquito [*Culex pipiens quinquefasciatus* (Say)]

Insecticidal activity is determined using third instar larvae of the mosquito *Culex pipiens quinquefasciatus*. Ten larvae are placed in a six ounce paper cup containing 100 milliliters of an aqueous solution of the test chemical. The treated larvae are stored at 70° F., and 48 hours later the mortality is recorded. Test concentrations range from 0.5 ppm down to that at which approximately 50% mortality occurs.

K. Two-spotted Mite [*Tetranychus urticae* (Koch)]

A pinto bean plant (*Phaseolus sp.*) approximately 10 centimeters tall is transplanted into sandy loam soil in a 3-inch clay pot and infested with two-spotted mites of mixed ages and sexes. Twenty-four hours later the infested plants are inverted and dipped for 2–3 seconds in a 50—50 acetone-water solution of the test compound. The treated plant is held in a greenhouse for seven days. Mortality is then determined for both the adult mites and the nymphs hatching from eggs which were on the plants at the time of treatment. The primary screening level for this test is 0.05% by weight of the test compound in the acetone-water solution.

| Symbols for Table II | | |
|---|---|---|
| HF | : | housefly |
| LB | : | Lygus bug |
| BA | : | black bean aphid |
| BAS | : | black bean aphid systemic |
| GPA | : | green peach aphid |
| GR | : | German cockroach |
| SCM | : | saltmarsh caterpillar |
| CL | : | cabbage looper |
| TBW | : | tobacco budworm |
| MOS | : | mosquito |
| 2SM | : | two-spotted mite - (1) adults (2) eggs (3) Sys |
| > | : | greater than |
| < | : | less than |
| — | : | not included in test |

TABLE II

| Compound Number | INSECTICIDAL ACTIVITY - APPROXIMATE LD$_{50}$ VALUES | | | | | | | | | | 2SM | | |
|---|---|---|---|---|---|---|---|---|---|---|---|---|---|
| | HF | BA | BAS | GPA | GR | LB | SMC | CL | TBW | MOS | Adults | Eggs | Sys |
| 1 | 35 | .03 | >10 | .03 | >.1 | >.05 | >.05 | >.1 | >.1 | 1 | <.045 | >.05 | >10 |
| 2 | 35 | .03 | >10 | .05 | >.1 | >.05 | >.05 | >.1 | >.1 | >1 | >.05 | >.05 | — |
| 3 | 19 | .0005 | >10 | .002 | .01 | >.05 | .05 | >.1 | .1 | >1 | <.05 | <.05 | >10 |
| 4 | 21 | .0005 | >10 | .003 | .05 | >.05 | >.05 | >.1 | .1 | >1 | >.05 | >.05 | — |
| 5 | 20 | .0003 | 2 | .0005 | .01 | >.05 | .05 | .01 | .02 | >1 | .05 | <.05 | >10 |
| 6 | >100 | .005 | >10 | .03 | >.1 | >.05 | >.05 | >.1 | >.1 | >1 | <.05 | <.05 | >10 |
| 7 | >100 | .005 | 1 | .03 | >.1 | >.05 | >.05 | >.1 | >.1 | >1 | >.05 | .05 | >10 |
| 8 | 100 | .002 | 10 | .005 | >.1 | >.05 | >.05 | >.1 | >.1 | >1 | .05 | <.05 | >10 |
| 9 | <100 >10 | .0008 <.05 | >10 | .05 | .1 | >.05 | >.05 | >.05 | >.05 | >1 | >.05 | >.05 | >10 |
| 10 | >100 | >.005 | — | — | — | — | — | — | >.05 | >1 | >.05 | >.05 | — |
| 11 | 100 | >.05 | — | — | — | — | — | — | >.05 | >1 | >.05 | .05 | — |
| 12 | >100 <100 | >.05 | — | — | — | — | — | — | >.05 | >1 | >.05 <.05 | >.05 | — |
| 13 | >10 | .005 | >10 | — | — | — | — | — | >.05 | >1 | >.005 | >.05 | >10 |
| 14 | >100 | .005 | >10 | — | — | — | — | — | >.05 | >1 | >.05 <.05 | >.05 <.05 | — |
| 15 | 100 | .003 | >10 | .002 | >.1 | >.05 | >.05 | >.05 | >.05 | >1 | >.005 <.05 | >.005 <.05 | >10 |
| 16 | >100 | .01 | >10 | .05 | >.1 | >.05 | >.05 | >.05 | .05 | >1 | >.005 | >.005 | — |
| 17 | >100 | >.05 | — | — | — | — | — | — | >.05 | >1 | >.05 | >.05 | — |
| 18 | >100 | >.05 | — | — | — | — | — | — | >.05 | >1 | >.05 | >.05 | — |

Table II is a summary of the results of tests performed on the compounds of Table I. These test results are expressed as LD$_{50}$ values, which represent the dose of test compound which was lethal to 50% of the insect population in the test. The entries in Table II were obtained as follows:

For a particular insect, each compound was initially tested at the primary screening level. Those compounds showing less than 50% kill at this level are represented in the table by the primary screening level preceded by a "greater than" sign (>). Those compounds showing approximately 50% kill are represented by the primary screening level alone. Those compounds showing greater than 50% kill were subjected to further testing at successively lower levels, until the level was found at which approximately 50% kill was achieved. The latter level is listed as the LD$_{50}$ for this group.

The primary screening level in each of the above tests was selected for purposes of convenience only, and none of the figures in the table are to be understood as representing the highest level at which a viable test for insecticidal activity can be conducted. Dashes are used in Table II where no tests were performed at all.

The amount of active compound of formulation which is considered to be insecticidally effective is that amount which, when applied to the pest habitat of feedstuff, will kill or substantially injure a significant portion residing or feeding thereon. The active compounds of this invention can be employed either as the sole pesticide compound of the formulations or as one of a mixture of compounds in the formulation having similar utility. Furthermore, the presently disclosed pesticide compositions need not be active as such. The purposes of this invention will be fully served by a composition which is rendered active by external influences, such as light, or by physiological action occurring when the preparation is ingested or penetrates into the body of the pest.

The precise manner in which the pesticide compounds of this invention are used in any particular instance will be readily apparent to a person skilled in the art. Generally, the active pesticidal compound will be used as a component of a liquid composition; for example, an emulsion, suspension, or aerosol spray. While the concentration of the active pesticide compound in the present formulation can vary within rather wide limits, ordinarily, the pesticide composition will comprise not more than about 80.0 percent by weight of the formulation.

The compositions of the invention are generally applied to the pest, pest habitat or feedstuff to be treated in an agricultural formulation which also comprises an agronomically acceptable carrier. By agronomically acceptable carrier is meant any substance which can be used to dissolve, disperse, or diffuse an active compound in the composition without impairing the effectiveness of the compound and which by itself has no detrimental effect on the soil, equipment, crops, or agronomic environment. The compositions of the invention can be either solid or liquid formulations or solutions. For example, the compounds can be formulated as wettable powders, emulsifiable concentrates, granulars and dusts. In such formulations, the compounds are extended with a liquid or solid carrier and; when desired, suitable surfactants are incorporated.

It is usually desirable to include adjuvants, such as wetting agents, spreading agents, dispersing agents, stickers, adhesives, and the like, in accordance with agricultural practices.

For the preparation of emulsifiable concentrates, the active compounds can be dissolved in organic solvents, such as benzene, toluene, xylene, methylated naphthalene, corn oil, pine oil, O-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent, soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product.

Wettable powders suitable for spraying, can be prepared by admixing the active compounds with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to about 80% by weight. A dispersing agent can constitute about 0.5% to about 3% of the composition, and a wetting agent can constitute from about 0.1% to about 5% of the composition.

Dusts can be prepared by mixing the composition of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to about 80% by weight of the active ingredients are commonly made and are subsequently diluted to about 1% to 10% use concentration.

The compounds of the invention can be applied as sprays by methods commonly employed, such as conventional high-gallonage hydraulic sprays, low gallonage sprays, air-blast spray, aerial sprays and dusts. For low volume applications, a solution of the active compounds is usually used. The dilution and rate of application will usually depend upon such factors as the type of equipment employed, the method of application, and the area to be treated.

For some applications, it may be useful to add one or more other insecticides to the compositions of the invention. Examples of other insecticides which can be incorporated to provide additional advantages include parathion, methyl parathion, malathion, carbaryl, methomyl dicofol, monocrotophos, chlordimeform, and the like. Other pesticides, including fungicides and plant bactericides can also be included in the compositions of the invention.

What is claimed is:

1. A compound of the formula

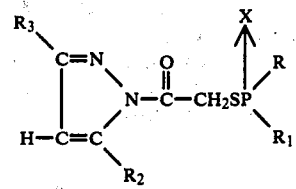

wherein X is oxygen or sulfur, R is selected from the group consisting of alkyl having 1 to 6 carbon atoms, inclusive, and alkoxy having 1 to 6 carbon atoms, inclusive; $R_1$ is alkoxy having 1 to 6 carbon atoms, inclusive; $R_2$ is selected from the group consisting of hydrogen and methyl; and $R_3$ is selected from the group consisting of hydrogen, methyl and phenyl.

2. A compound according to claim 1 wherein X is oxygen, R is alkoxy, $R_2$ is methyl and $R_3$ is methyl.

3. A compound according to claim 2 wherein R is ethoxy and $R_1$ is ethoxy.

4. A compound according to claim 1 wherein X is oxygen, R is alkoxy, $R_2$ is hydrogen and $R_3$ is methyl.

5. A compound according to claim 4 wherein R is ethoxy and $R_1$ is ethoxy.

6. A compound according to claim 1 wherein X is sulfur, R is alkoxy, $R_2$ is methyl and $R_3$ is methyl.

7. A compound according to claim 6 wherein R is ethoxy and $R_1$ is ethoxy.

8. A compound according to claim 6 wherein R is methoxy and $R_1$ is methoxy.

9. A compound according to claim 1 wherein X is sulfur, R is alkyl, $R_2$ is methyl and $R_3$ is methyl.

10. A compound according to claim 9 wherein R is ethyl and $R_1$ is ethoxy.

11. A compound according to claim 9 wherein R is ethyl and $R_1$ is isopropoxy.

12. A compound according to claim 9 wherein R is ethyl and $R_1$ is isobutoxy.

13. A compound according to claim 1 wherein X is sulfur, R is alkyl, $R_2$ is hydrogen and $R_3$ is methyl.

14. A compound according to claim 13 wherein R is ethyl and $R_1$ is ethoxy.

15. A compound according to claim 13 wherein R is ethyl and $R_1$ is isopropoxy.

16. A compound according to claim 13 wherein R is ethyl and $R_1$ is isobutoxy.

17. A compound according to claim 1 wherein X is sulfur, R is alkoxy, $R_2$ is hydrogen and $R_3$ is methyl.

18. A compound according to claim 17 wherein R is methoxy and $R_1$ is methoxy.

19. A compound according to claim 17 wherein R is ethoxy and $R_1$ is ethoxy.

20. A compound according to claim 1 wherein X is sulfur, R is alkyl, $R_2$ is methyl and $R_3$ is phenyl.

21. A compound according to claim 20 wherein R is ethyl and $R_1$ is ethoxy.

22. A compound according to claim 20 wherein R is ethyl and $R_1$ is isopropoxy.

23. A compound according to claim 20 wherein R is ethyl and $R_1$ is isobutoxy.

24. A compound according to claim 1 wherein X is sulfur, R is alkoxy, $R_2$ is methyl and $R_3$ is phenyl.

25. A compound according to claim 24 wherein R is ethoxy and $R_1$ is ethoxy.

26. A compound according to claim 24 in which R is methoxy and $R_1$ is methoxy.

27. A compound according to claim 1 wherein X is oxygen, R is alkoxy, $R_2$ is methyl and $R_3$ is phenyl.

28. A compound according to claim 27 in which R is ethoxy and $R_1$ is ethoxy.

29. A insecticidal composition comprising
(a) less than about 80 percent by weight of a compound having the formula

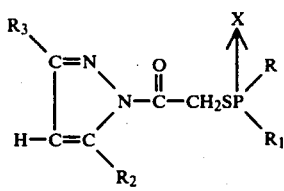

wherein X is oxygen or sulfur, R is selected from the group consisting of alkyl having 1 to 6 carbon atoms, inclusive, and alkoxy having 1 to 6 carbon atoms, inclusive; $R_1$ is alkoxy having 1 to 6 carbon atoms, inclusive; $R_2$ is selected from the group consisting of hydrogen and methyl; and $R_3$ is selected from the group consisting of hydrogen, methyl and phenyl; and (b) an agronomically acceptable carrier.

30. The method of controlling insects comprising applying to said insect, insect habitat or feedstuff of said insect an insecticidally effective amount of a compound having the formula

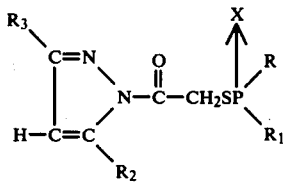

wherin X is oxygen or sulfur, R is selected from the group consisting of alkyl having 1 to 6 carbon atoms, inclusive, and alkoxy having 1 to 6 carbon atoms, inclusive; $R_1$ is alkoxy having 1 to 6 carbon atoms, inclusive; $R_2$ is selected from the group consisting of hydrogen and methyl; and $R_3$ is selected from the group consisting of hydrogen, methyl and phenyl.

31. The method according to claim 30 wherein X is oxygen, R is alkoxy, $R_2$ is methyl and $R_3$ is methyl.

32. The method according to claim 31 wherein R is ethoxy and $R_1$ is ethoxy.

33. The method according to claim 30 wherein X is oxygen, R is alkoxy, $R_2$ is hydrogen and $R_3$ is methyl.

34. The method according to claim 33 wherein R is ethoxy and $R_1$ is ethoxy.

35. The method according to claim 30 wherein X is sulfur, R is alkoxy, $R_2$ is methyl and $R_3$ is methyl.

36. The method according to claim 35 wherein R is ethoxy and $R_1$ is ethoxy.

37. The method according to claim 35 wherein R is methoxy and $R_1$ is methoxy.

38. The method according to claim 30 wherein X is sulfur, R is alkyl, $R_2$ is methyl and $R_3$ is methyl.

39. The method according to claim 38 wherein R is ethyl and $R_1$ is ethoxy.

40. The method according to claim 38 wherein R is ethyl and $R_1$ is isopropoxy.

41. The method according to claim 38 wherein R is ethyl and $R_1$ is isobutoxy.

42. The method according to claim 30 wherein X is sulfur, R is alkyl, $R_2$ is hydrogen and $R_3$ is methyl.

43. The method according to claim 42 wherein R is ethyl and $R_1$ is ethoxy.

44. The method according to claim 42 wherein R is ethyl and $R_1$ is isopropoxy.

45. The method according to claim 42 wherein R is ethyl and $R_1$ is isobutoxy.

46. The method according to claim 30 wherein X is sulfur, R is alkoxy, $R_2$ is hydrogen and $R_3$ is methyl.

47. The method according to claim 46 wherein R is methoxy and $R_1$ is methoxy.

48. The method according to claim 46 wherein R is ethoxy and $R_1$ is ethoxy.

49. The method according to claim 40 wherein X is sulfur, R is alkyl, $R_2$ is methyl and $R_3$ is phenyl.

50. The method according to claim 49 wherein R is ethoxy and $R_1$ is ethoxy.

51. The method according to claim 49 wherein R is ethyl and $R_1$ is isopropoxy.

52. The method according to claim 49 wherein R is ethyl and $R_1$ is isobutoxy.

53. The method according to claim 30 wherein X is sulfur, R is alkoxy, $R_2$ is methyl and $R_3$ is phenyl.

54. The method according to claim 53 wherein R is ethoxy and $R_1$ is ethoxy.

55. The method according to claim 53 wherein R is methoxy and $R_1$ is methoxy.

56. The method according to claim 30 wherein X is oxygen, R is alkoxy, $R_2$ is methyl and $R_3$ is phenyl.

57. The method according to claim 56 wherein R is ethoxy and $R_1$ is ethoxy.

* * * * *